United States Patent [19]

Lee

[11] Patent Number: 4,937,259
[45] Date of Patent: Jun. 26, 1990

[54] ANTIHYPERCHOLESTEROLEMIC COMPOUNDS

[75] Inventor: Ta JYH. Lee, Lansdale, Pa.

[73] Assignee: Merck & Co., Inc., Rahway, N.J.

[21] Appl. No.: 363,816

[22] Filed: Jun. 9, 1989

[51] Int. Cl.$^5$ .................. A61K 31/365; C07D 309/30
[52] U.S. Cl. ..................... 514/460; 549/292;
514/459; 514/252; 514/255; 514/325; 514/423;
546/204; 546/196; 548/525; 544/374; 544/375
[58] Field of Search ................ 549/292; 514/459, 460,
514/824, 252, 255, 325, 423; 544/374, 375;
546/196, 204; 548/525

[56] References Cited

U.S. PATENT DOCUMENTS

| | | | |
|---|---|---|---|
| 4,448,979 | 5/1984 | Terahara et al. | 549/292 |
| 4,517,373 | 5/1985 | Terahara et al. | 549/292 |
| 4,537,859 | 8/1985 | Terahara et al. | 435/136 |
| 4,604,472 | 8/1986 | Ide et al. | 549/292 |
| 4,733,003 | 3/1988 | Ide et al. | 560/119 |
| 4,855,456 | 8/1989 | Lee et al. | 549/292 |

FOREIGN PATENT DOCUMENTS 2075013 11/1981 United Kingdom ............... 549/292

Primary Examiner—Glennon H. Hollrah
Assistant Examiner—Mark W. Russell
Attorney, Agent, or Firm—Melvin Winokur; Joseph F. DiPrima

[57] ABSTRACT

Compounds of Formula (I) and (II):

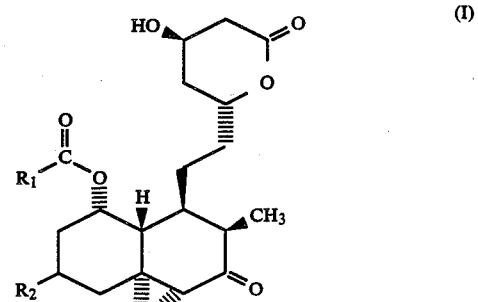

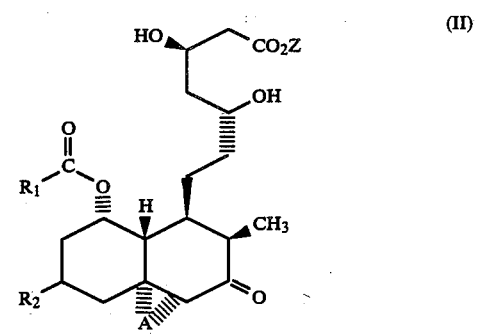

are HMG-CoA reductase inhibitors.

8 Claims, No Drawings

ANTIHYPERCHOLESTEROLEMIC COMPOUNDS

BACKGROUND OF THE INVENTION

Hypercholesterolemia is known to be one of the prime risk factors for ischemic cardiovascular disease, such as arteriosclerosis. Bile acid sequestrants have been used to treat this condition; they seem to be moderately effective but they must be consumed in large quantities, i.e. several grams at a time and they are not very palatable.

MEVACOR® (lovastatin), now commercially available, is one of a group of very active antihypercholesterolemic agents that function by limiting cholesterol biosynthesis by inhibiting the enzyme, HMG CoA reductase. In addition to the natural fermentation products, mevastatin and lovastatin, there are a variety of semi-synthetic and totally synthetic analogs thereof.

The naturally occurring compounds and their semi-synthetic analogs have the following general structural formulae:

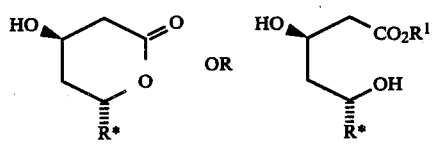

wherein:
$R^1$ is hydrogen, $C_{1-5}$ alkyl or $C_{1-5}$ alkyl substituted with a member of the group consisting of phenyl, dimethylamino, or acetylamino;

U.S. Pat. No. 4,517,373 discloses semi-synthetic hydroxy containing compounds represented by the above general formula wherein $R^*$ is

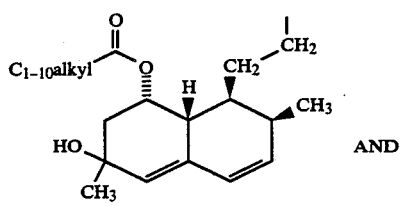

U.S. Pat. No. 4,537,859 and U.S. Pat. No. 4,448,979 also disclose semi-synthetic hydroxy-containing compounds represented by the above general formula wherein $R^*$ is

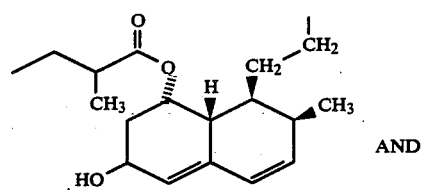

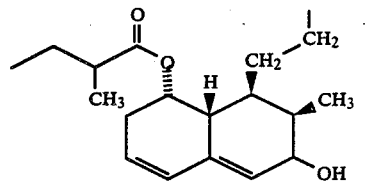

These compounds are prepared by the action of certain microorganisms on the corresponding non-hydroxylated substrates. One such organism described in U.S. Pat. No. 4,537,859 is of the genus Nocardia.

U.K. Pat. No. 2,075,013 discloses semi-synthetic hydroxy containing compounds represented by the above general formula wherein $R^*$ is:

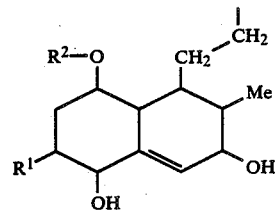

wherein $R^1$ is H or Me, and $R^2$ is H or acyl.

U.S. patent application Ser. No. 254,525 filed Oct. 6, 1988 discloses 6-substituted compounds of the above general formula wherein $R^*$ is:

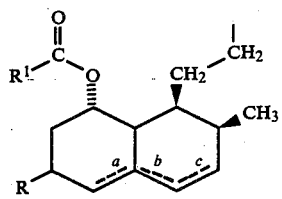

wherein R is

and $R^1$, $R^4$, $R^7$, $R^8$ and $R^9$ are broadly defined organic moieties.

U.S. Pat. Nos. 4,604,472 and 4,733,003 disclose compounds of the above formula wherein $R^*$ is:

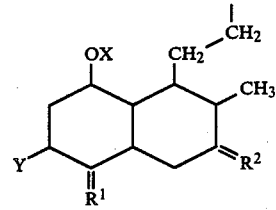

wherein X represents a hydrogen atom or a 2-methylbutyryl group, Y represents a hydrogen atom or a methyl group and $R^1$ and $R^2$ are the same or different and each represents an oxygen atom or a group of formula $=N-OR^3$ where $R^3$ is a hydrogen or alkyl moiety.

Copending U.S. patent application Ser. No. 161,579 filed Feb. 29, 1988 now U.S. Pat. No. 4,855,456 discloses epoxide containing compounds wherein R* is:

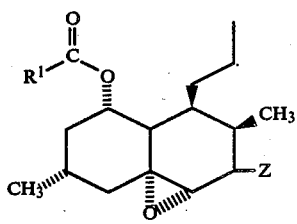

Z is I, Br or Cl.

Copending U.S. patent application Ser. No. 161,529 filed Feb, 29, 1988 discloses hydroxy containing compounds of the above general formula wherein R* is:

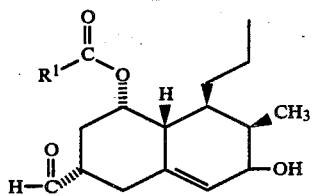

DETAILED DESCRIPTION OF THE INVENTION

This invention relates to HMG-CoA reductase inhibitors of formulae (I) and (II):

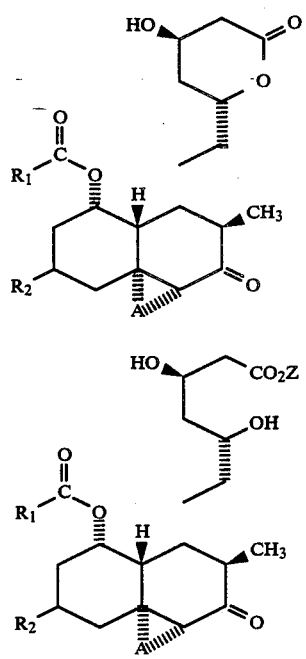

wherein:

$R_1$ is:
(1) $C_{1-10}$ alkyl;
(2) substituted $C_{1-10}$ alkyl in which one or more substituent(s) is selected from:
 (a) halogen,
 (b) hydroxy,
 (c) $C_{1-10}$ alkoxy,
 (d) $C_{1-5}$ alkoxycarbonyl,
 (e) $C_{1-5}$ acyloxy,
 (f) $C_{3-8}$ cycloalkyl,
 (g) phenyl,
 (h) substituted phenyl in which the substituents are X and Y,
 (i) $C_{1-10}$ alkylS(O)$_n$,
 (j) $C_{3-8}$ cycloalkylS(O)$_n$,
 (k) phenylS(O)$_n$,
 (l) substituted phenylS(O)$_n$ in which the substituents are X and Y, and
 (m) oxo;
 (n) nitrile,
 (o) $NR_3R_4$,
 (p) $CONR_3R_4$
(3) $C_{1-10}$ alkoxy;
(4) $C_{2-10}$ alkenyl;
(5) $C_{3-8}$ cycloalkyl;
(6) substituted $C_{3-8}$ cycloalkyl in which one substituent is
 (a) $C_{1-10}$ alkyl
 (b) substituted $C_{1-10}$ alkyl in which the substituent is
  (i) halogen,
  (ii) hydroxy,
  (iii) $C_{1-10}$ alkoxy,
  (iv) $C_{1-5}$ alkoxycarbonyl,
  (v) $C_{1-5}$ acyloxy,
  (vi) phenyl,
  (vii) substituted phenyl in which the substituents are X and Y
  (viii) $C_{1-10}$ alkylS(O)$_n$,
  (ix) $C_{3-8}$ cycloalkylS(O)$_n$,
  (x) phenylS(O)$_n$,
  (xi) substituted phenylS(O)$_n$ in which the substituents are X and Y, and
  (xii) oxo,
 (c) $C_{1-10}$ alkylS(O)$_n$,
 (d) $C_{3-8}$ cycloalkylS(O)$_n$,
 (e) phenylS(O)$_n$,
 (f) substituted phenylS(O)$_n$ in which the substituents are X and Y,
 (g) halogen,
 (h) hydroxy,
 (i) $C_{1-10}$ alkoxy,
 (j) $C_{1-5}$ alkoxycarbonyl,
 (k) $C_{1-5}$ acyloxy,
 (l) phenyl, and
 (m) substituted phenyl in which the substituents are X and Y;
(7) phenyl;
(8) substituted phenyl in which the substituents are X and Y;
(9) amino;
(10) $C_{1-5}$ alkylamino;
(11) di($C_{1-5}$ alkyl)amino;
(12) phenylamino;
(13) substituted phenylamino in which the substituents are X and Y;
(14) phenyl $C_{1-10}$ alkylamino;
(15) substituted phenyl $C_{1-10}$ alkylamino in which the substituents are X and Y;
(16) a member selected from the group consisting of:
 (a) piperidinyl,
 (b) pyrrolidinyl,
 (c) piperazinyl, R₂ is H or CH₃;
R₃ and R₄ are independently selected from:
(a) C₁₋₅ alkyl;
(b) substituted phenyl in which the substituents are X and Y,
A is

or O;
X and Y are independently selected from:
(a) OH;
(b) halogen,
(c) trifluoromethyl,
(d) C₁₋₃alkoxy,
(e) C₁₋₃alkylcarbonyloxy,
(f) phenylcarbonyloxy,
(g) C₁₋₃alkoxycarbonyl,
(h) phenyloxycarbonyl,
(i) hydrogen,
(J) C₁₋₅alkyl;
Z is selected from
(1) hydrogen;
(2) C₁₋₅alkyl;
(3) substituted C₁₋₅ in which the substituent is selected from
  (a) phenyl,
  (b) dimethylamino, and
  (c) acetylamino, and
(4) 2,3 dihydroxypropyl; halogen is Cl or F; n is 0, 1 or 2; and a pharmaceutically acceptable salt thereof.

Except where specifically defined to the contrary, the terms "alkyl", "alkenyl", "acyl" "aryloxy" and "alkoxy" include both the straight-chain and branched-chain species of the term.

One embodiment of this invention is the class of compounds of formulae (I) and (II) wherein:
R₁ is selected from:
(1) C₁₋₁₀ alkyl;
(2) substituted C₁₋₁₀ alkyl in which one or more substituent(s) is selected from
  (a) halogen,
  (b) hydroxy,
  (c) C₁₋₁₀ alkoxy,
  (d) C₁₋₅ alkoxycarbonyl,
  (e) C₁₋₅ acyloxy,
  (f) C₃₋₈ cycloalkyl,
  (g) phenyl,
  (h) substituted phenyl in which the substituents are X and Y,
  (i) C₁₋₁₀alkyl S(O)ₙ,
  (j) nitrile,
  (k) NR₃R₄,
  (l) CONR₃R₄,
  (m) oxo;
(3) C₃₋₈ cycloalkyl;
(4) substituted C₃₋₈ cycloalkyl in which one substituent is selected from
  (a) C₁₋₁₀ alkyl,
  (b) substituted C₁₋₁₀ alkyl in which the substituent is selected from
    (i) halogen,
    (ii) hydroxy,
    (iii) C₁₋₁₀ alkoxy
    (iv) C₁₋₅ acyloxy,
    (v) C₁₋₅ alkoxycarbonyl,
    (vi) phenyl,
    (vii) substituted phenyl in which the substituents are X and Y, and
    (viii) oxo,
  (c) halogen,
  (d) hydroxy,
  (e) C₁₋₁₀ alkoxy,
  (f) C₁₋₅ alkoxycarbonyl,
  (g) C₁₋₅ acyloxy,
  (h) phenyl,
  (i) substituted phenyl in which the substituents are X and Y;
(5) phenylamino;
(6) substituted phenylamino in which the substituents are X and Y;
(7) phenyl C₁₋₁₀alkylamino; and
(8) substituted phenyl C₁₋₁₀ alkylamino in which the substituents are X and Y,
(9) C₂₋₁₀alkenyl;
X and Y independently are:
(a) OH,
(b) F,
(c) trifluoromethyl,
(d) C₁₋₃alkoxy,
(e) hydrogen,
(f) C₁₋₅alkyl.

In one class of this embodiment are the compounds of formula (I) and (II) wherein:
R₁ is C₁₋₁₀alkyl,
R₂ is CH₃, and
A is

Illustrating this class are the following compounds:
(1) 6(R) [2-[2(R),6(S) dimethyl-8(S)-(2,2-dimethyl-butyryloxy)-α-4,4a-methyleno-1,2,3,4,4a,5,6,7,8,8a(R)-decahydro-3-oxo-naphthyl-1(S)]ethyl]-4(R)-hydroxy-3,4,5,6-tetrahydro-2H-pyran-2-one;
(2) 6(R)-[2-[2(R),6(S)-dimethyl-8(S)-(2-methyl-butyryloxy)-α-4,4a-methyleno-1,2,3,4,4a,5,6,7,8,8a(R)-decahydro-3-oxo-naphthyl-1(S)]ethyl]-4(R)-hydroxy-3,4,5,6-tetrahydro-2H-pyran-2-one; and the corresponding dihydroxy acids and esters thereof.

The compounds of formula (I) are prepared from lovastatin, simvastatin or mevastatin following the outline in Scheme 1.

SCHEME 1

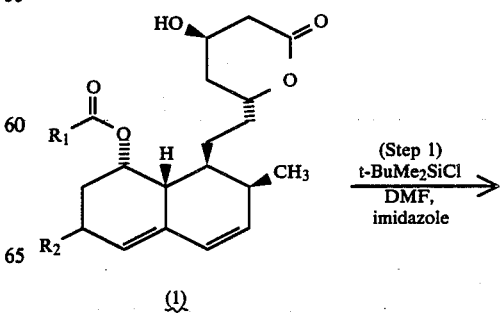

(Step 1)
t-BuMe₂SiCl
DMF,
imidazole (1)

SCHEME 1 -continued

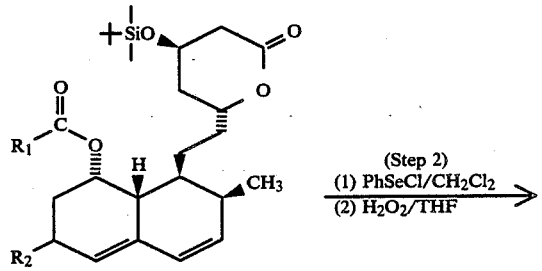

(2)

(Step 2)
(1) PhSeCl/CH$_2$Cl$_2$
(2) H$_2$O$_2$/THF

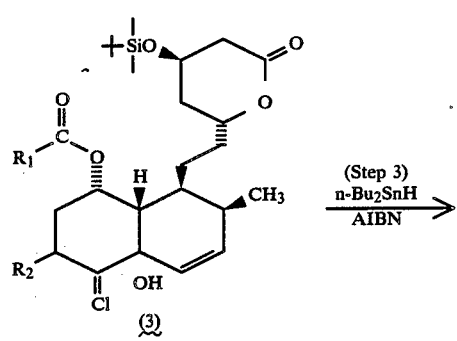

(3)

(Step 3)
n-Bu$_2$SnH
AIBN

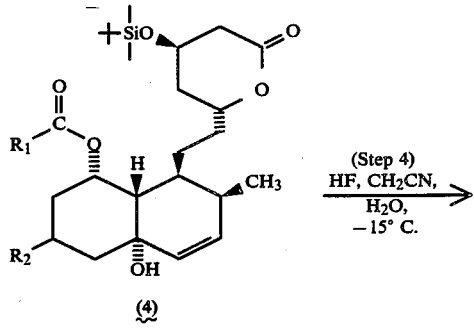

(4)

(Step 4)
HF, CH$_2$CN,
H$_2$O,
−15° C.

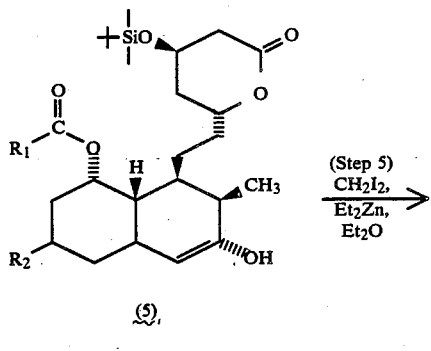

(5)

SCHEME 1 -continued

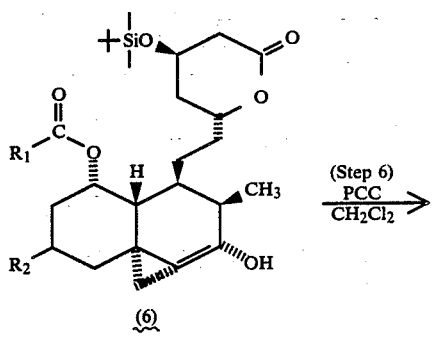

(6)

(Step 6)
PCC
CH$_2$Cl$_2$

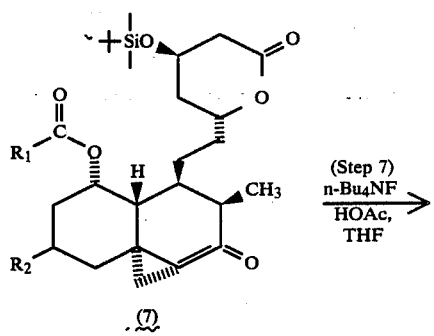

(7)

(Step 7)
n-Bu$_4$NF
HOAc,
THF

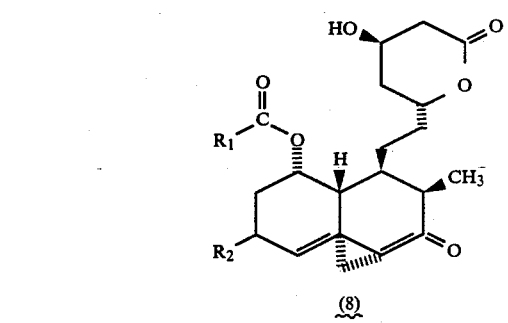

(8)

Starting material (1) is treated with a reagent suitable for protecting the alcohol group at the lactone 4-position. Examples of suitable reagents are trialkylsilyl chlorides, dialkylarylsilyl chlorides and dihydropyran.

The diene (2) of step (B) is treated with a halogenating agent such as phenylselenyl chloride or bromide or phenylsulfinyl chloride, preferably phenylselenyl chloride, in an approximately equimolar ratio in an inert solvent at about −80° C., for approximately 20 minutes; illustrative of such inert solvents are methylene chloride, ether and the like. After a standard workup the product residue is dissolved in an ethereal solvent, chilled to about 0° C. and oxidized with an agent such as 30% hydrogen peroxide or a peroxy acid such as peroxybenzoic acid to yield a halohydrin analog (3).

Intermediate (3) is treated with a halide reducing agent such as a trialkyltin hydride or a triaryltin hydride, preferably tri n-butyltin hydride and a radical initiator such as azobisisobutyronitrile (AIBN) in an inert solvent such as benzene at a temperature between 70° C. and 100° C. preferably about 90° C. for 0.5 to 5 hours preferably 2 hours, to yield intermediate (4).

Intermediate (4) is treated with an aqueous acidic mixture such as approximately 48% HF or perchloric acid in a polar solvent such as acetonitrile or aqueous acetone at a temperature between −20° C. and 10° C., preferably 48% HF/CH$_3$CN at about −15° C., to yield compound (5).

Compound (5) is treated with diethylzinc and diiodomethane in a etheral solvent at ambient temperature for about 1 hour followed by refluxing for 2 hours to yield compound (6).

Compound (6) is reacted with pyridinium chlorochromate (PCC) in CH$_2$Cl$_2$ to yield the 3-keto compound (7).

The silyl or tetrahydropyranyl protecting group of compound (7) is removed by treatment with a tetrabutylammonium fluoride in a mixture of THF/acetic acid to yield product (8).

Starting compounds (1) wherein the acyl side chain is other than 2-methylbutryloxy are prepared from lovastatin by hydrolysis of the 8-acyl side chain, following the procedure in U.S. Pat. No. 4,444,784, followed by acylation with an appropriate alkanoyl chloride in the presence of lithium bromide and dimethylaminopyridine in pyridine using the Procedure in copending U.S. application Ser. No. 038,580 filed Apr. 15, 1987. Alternatively, the acylation is conducted with an alkanoyl chloride or an alkanoic acid under standard reaction conditions. The alkanoyl chloride can be formed by standard chemical transformations such as substitution with an alkyl moiety or other appropriate electrophile at an acidic C-H site on an available starting material.

Where A in the structure for formula (I) is oxygen, the epoxide moiety may be introduced by employing m-chloroperoxybenzoic acid in Step 5, in place of CH$_2$I$_2$/Et$_2$Zn.

Where the reaction conditions of the above noted chemical transformations would be deleterious to the substituents in the 8 acyloxy moiety, the acetoxy group can be employed as a protecting group which after the elaboration of the naphthyl ring can be removed by hydrolysis to give the 8-hydroxy derivative which then can be acylated according to the general procedures described in U.S. Pat. No. 4,661,483.

Where the product formed by the above described synthetic pathways is not the desired form of that compound, then that product may be subjected to one or more further reactions such as hydrolysis, disilylation, ammonolysis or lactonization by conventional methods.

Preferred metal salts are salts with alkali metals, such as sodium or potassium, salts with alkaline earth metals, such as calcium, or salts with other metals such as magnesium, aluminum, iron, zinc, copper, nickel or cobalt, of which the alkali metal, alkaline earth metal, magnesium and aluminum salts are preferred, the sodium, calcium and aluminum salts being most preferred.

Preferred amino acids to form amino acide salts are basic amino acids, such as arginine, lysine, a,β-diaiminobutyric acid or ornithine.

Preferred amines to form amine salts include t-octylamine, dibenzylamine, ethylenediamine, morpholine, and tris(hydroxymethyl)aminomethane. Also preferred is ammonia to form the ammonium salt.

Esters are preferably the alkyl esters, such as the methyl, ethyl, propyl, isopropyl, butyl, isobutyl, or pentyl esters, of which the methyl ester is preferred. However, other esters such as phenyl-C$_{1-5}$alkyl may be employed if desired.

Metal salts of the carboxylic acids of formula (II) may be obtained by contacting a hydroxide, carbonate or similar solvent with the carboxylic acid of formula (II).

The aqueous solvent employed is preferably water, or it may be a mixture of water with an organic solvent, preferably an alcohol (such as methanol or ethanol), a ketone (such as acetone), an aliphatic hydrocarbon (such as hexane) or an ester (such as ethyl acetate). It is preferred to use a mixture of a hydrophilic organic solvent with water. Such reactions are normally conducted at ambient temperature but they may, if desired, be conducted with heating or cooling.

Amine salts of the carboxylic acids of formula (II) may be obtained by contacting an amine in an aqueous solvent with the carboxylic acid of formula (II). Suitable aqueous solvents include water and mixtures of water with alcohols (such as methanol or ethanol), ethers (such as diethyl ether and tetrahydrofuran), nitriles (such as acetonitrile) or ketones (such as acetone); it is preferred to use aqueous acetone as the solvent for this reaction. The reaction is preferably carried out at a temperature of ambient or below, more preferably a temperature of from 5° to 10° C. The reaction immediately goes to completion. Alternatively, a metal salt of the carboxylic acid of formula (II) (which may have been obtained as described above) can be dissolved in an aqueous solvent, after which a mineral acid salt (for example the hydrochloride) of the desired amine is added, employing the same reaction conditions as when the amine itself is reacted with the carboxylic acid of formula (II) and the desired product is then obtained by metathesis.

Amino acid salts of the carboxylic acids of formula (II) may be obtained by contacting an amino acid in aqueous solution with the carboxylic acid of formula (II). Suitable aqueous solvents include water and mixtures of water with alcohols (such as methanol or ethanol) or ethers (such as tetrahydrofuran).

Esters, preferably alkyl esters, of the carboxylic acids of formula (II) may be obtained by contacting the carboxylic acid of formula (II) with an appropriate alcohol, preferably in the presence of an acid catalyst, for example, a mineral acid (such as hydrochloric acid or sulphuric acid), a Lewis acid (for example boron trifluoride) or an acidic ion exchange resin. The solvent employed for this reaction is not critical, provided that it does not adversely affect the reaction., suitable solvents include the alcohol itself, benzene, chloroform, ethers and the like. Alternatively, the desire product may be obtained by contacting the carboxylic acid of formula (II) with a diazoalkane, in which the alkane moiety may be substituted or unsubstituted. This reaction is usually effected by contacting the acid with an ethereal solution of the diazoalkane. As a further alternative, the ester may be obtained by contacting a metal salt of the carboxylic acid of formula (II) with a halide, preferably an alkyl halide, in a suitable solvent; preferred solvents include dimethylformamide, tetrahydrofuran, dimethylsulfoxide and acetone. Finally, esters may also be obtained from the lactone of formula (I) by reaction with an appropriate alkoxide in an absolute alkanol. All of the reactions for producing esters are preferably effected at about ambient temperature, but, if required by the nature of the reaction system, the reactions may be conducted with heating or cooling.

Lactones of the carboxylic acids of formula (I) may be obtained by lactonizing the carboxylic acids of formula (II) under ordinary conditions known to one skilled in the art.

The intrinsic HMG-CoA reductase inhibition activity of the claimed compounds is measured in the in vitro protocol published in *J. Med. Chem.*, 28, p. 347–358 (1985).

For estimation of relative inhibitory potencies, compactin (i.e., mevastatin) was assigned a value of 100 and the $IC_{50}$ value of the test compound was compared with that of compactin determined simultaneously in the published in vitro protocol. Illustrative of the relative potency of the claimed compounds is that exhibited by the compound of Example 1 which has a relative potency of 186.

The compounds of this invention are useful as antihypercholesterolemic agents for the treatment of arteriosclerosis, hyperlipidemia, familial hypercholesterolemia and like diseases in humans. They may be administered orally or parenterally in the form of a capsule, a tablet, an injectable preparation or the like. It is usually desirable to use the oral route. Doses may be varied, depending on the age, severity, body weight and other conditions of human patients but daily dosage for adults is within a range of from about 10 mg to 2000 mg (preferably 10 to 100 mg) which may be given in two to four divided doses.

The compounds of this invention may also be coadministered with pharmaceutically acceptable nontoxic cationic polymers capable of binding bile acids in a non-reabsorbable form in the gastrointestinal tract. Examples of such polymers include cholestyramine, coletipol and poly[methyl-(3-trimethylaminopropyl)iminotrimethylene dihalide]. The relative amount of the compounds of this invention and these polymers is between 1:100 and 1:15,000.

Included within the scope of this invention is the method of treating arteriosclerosis, familial hypercholesterolemia or hyperlipidemia which comprises administering to a subject in need of such treatment a nontoxic, therapeutically-effective amount of the compounds of formulae (I) or (II) of pharmaceutical compositions thereof.

The following examples illustrate the preparation of the compounds of the formulae (I) and (II) and their incorporation into pharmaceutical compositions and as such are not to be considered as limiting the invention set forth in the claims appended hereto:

EXAMPLE 1

Preparation of 6(R)-[2-[2(R),6(S)-dimethyl-8(S)-(2,2-dimethylbutyryloxy)-α-4,4a-methyleno-1,2,3,4,4a,5,6,7,8,8a(R)-decahydro-3-oxo-naphthyl-1(S)]ethyl]-4(R)-hydroxy-3,4,5,6-tetrahydro-2H-pyran-2-one (8')

Step 1: 6(R)-[2-[8(S)-(2,2-Dimethylbutyryloxy)-2(S),6(R)-dimethyl-1,2,6,7,8,8a(R)-hexahydro-naphthyl-1(S)]-ethyl]-4(R)-(t-butyldimethylsilyloxy)-3,4,5,6-tetrahydro-2H-pyran-2-one (2')

Tert-Butyldimethylsilyl chloride (8 g, 52 mmol) was added to a stirred solution of 6(R)-[2-[8(S)-(2,2-Dimethylbutyryloxy)-2(S),6(R)-dimethyl-1,2,6,7,8,8a(R)-hexahydronaphthyl-1(S)]ethyl]-4(R)-hydroxy-3,4,5,6-tetrahydro-2H-pyran-2-one (20 g, 48 mmol) and imidazole (6.8 g, 0.1 mol) in DMF (150 mL) at 0° C. The resulting mixture was stirred at 0° C. for 5 minutes, then warmed to room temperature and stirred for 5 hours. TLC analysis of an aliquot indicated that the reaction was complete. The reaction mixture was poured into cold water and extracted with ether. The ethereal extract was washed with dilute hydrochloric acid, water and 5% sodium bicarbonate solution. After drying over $MgSO_4$, the organic extract was filtered and the filtrate was concentrated in vacuo to afford the desired product as a colorless, viscous oil: NMR ($CDCl_3$) δ 0.84 (3H, t, J=7 Hz), 0.89 (3H, d, J=7 Hz), 0.90 (9H,s), 1.09 (3H, d, J=7 Hz), 1.11 (3H, s), 1.12 (3H, s), 4.30 (H, m), 4.60 (H, m), 5.33 (H, m), 5.51 (H, m), 5.77 (H, d of d, J=10, 6 Hz), 5.98 (H, d, J=10 Hz).

Step 2: 6(R)-[2-[5(S)-Chloro-4a(S)-hydroxy-8(S)-(2,2-dimethylbutyryloxy)-2(S),6(R)-dimethyl-1,2,-4a,5,6,7,8,8a(S)-octahydronaphthyl-1(S)]-ethyl]-4-(R)-(t-butyldimethylsilyloxy)-3,4,5,-6-tetrahydro-2H-pyran-2-one (3')

A solution of Phenylselenyl chloride (10 g, 52 mmol) in methylene chloride (50 mL) was added dropwise to a stirred solution of compound 2' (25.2 g, 48 mmol) in methylene chloride (350 mL) cooled in a dry ice/i-propanol bath (−78° C.). The resulting mixture was stirred at −78° C. for 20 minutes, poured into cold water (300 mL) and extracted with ether twice (400 mL, then 150 mL). The combined extracts were dried ($MgSO_4$), filtered and concentrated to afford an oily residue which was dissolved in tetrahydrofuran (300 mL). This solution was chilled in an ice bath (0° C.), and 30% hydrogen peroxide (15 mL) was added. The resulting mixture was stirred at 0° C. for 5 minutes, then warmed to room temperature and stirring continued for 1 hour. The reaction mixture was poured into cold water and extracted with chloroform three times (400 mL, then 2×100 mL). The combined extracts were dried ($MgSO_4$), filtered and concentrated to yield a residue which was purified by flash chromatography on a silica gel column. Elution with hexane:ethyl acetate (5:1/v:v) removed the impurities. Further elution with hexane:ethyl acetate (4:1/v:v) provided the title compound as a pale yellow gum which later solidified on standing.. mp 117°-8° C., NMR ($CDCl_3$) δ 0.075 (3H, s), 0.08 (3H, s), 0.85 (3H, t, J=7 Hz), 0.88 (9H, s), 0.89 (3H, d, J=7 Hz), 1.15 (3H, s), 1.16 (3H, s), 1.32 (3H, d, J=7 Hz), 1.58 (2H, q, J=7 Hz), 3.39 (H, s), 4.05 (H, bs), 4.30 (H, m), 4.60 (H, m), 5.32 (H, m), 5.59 (H, d, J=11 Hz), 5.79 (H, d of d, J=11, 6 Hz).

Anal. Calcd. for $C_{31}H_{53}ClO_6Si$: C, 63.61; H, 9.13. Found: C, 63.80; H, 9.04.

Step 3: 6(R)-[2-[4a(S)-hydroxy-8(S)-(2,2-dimethylbutyryloxy)-2(S),6(R)-dimethyl-1,2,4a,5,6,-7,8,8a(S)-octahydronaphthyl-1(S)]ethyl]-4(R)-(t-butyldimethylsilyloxy)-3,4,5,6-tetrahydro-2H-pyran-2-one (4')

Tributyltin hydride (7.06 ml, 26.25 mmol) and azobisisobutyronitrile (AIBN) (0.82 g, 5.0 mmol) were added to a magnetically stirred solution of chlorohydrin 3' (8.78 g, 15 mmol) in benzene (100 ml). The resulting solution was refluxed for 2 hours, cooled and concentrated in vacuo to a viscous yellow oil which was stirred with pet ether (200 ml) at −15° C. (ice/acetone bath) to provide 4' as a fluffy, colorless solid (6.9 g, mp 97°-9° C.). The filtrate was extracted with $CH_3CN$ (4×50 ml) to remove all of the product contained in the pet ether. The $CH_3CN$ extracts were combined and concentrated to a colorless oil which was purified by flash chromatography on a silica gel column. Elution with ethyl acetone/hexane (1:3/v:v) gave a colorless solid which was stirred in pet ether (25 ml) at 0° C. to remove some tin residues. The mixture was filtered to provide the product 4' as a colorless solid. M.P. 103°-4° C., nmr ($CDCl_3$) δ 0.07 (3H, s), 0.08 (3H,s), 0.88 (9H, s), 1.15 (3H, s), 1.16 (3H, s), 1.20 (3H, d, J=7 Hz), 2.78 (H, s), 4.28 (H, m), 4.58 (H, m), 5.30 (H, m), 5.58 (H, d, J=10 Hz), 5.67 (H, dd, J=10, 5 Hz).

Anal. Calcd. for $C_{31}H_{54}O_6Si$: C, 67.59; H, 9.88. Found: C, 67.20; H, 9.99.

Step 4: Preparation of 6(R)-[2-[3(S)-hydroxy-8(S)-(2,2-dimethylbutyryloxy)-2(R),6(S)-dimethyl-1,2,3,5,6,7,8,8a(R)-octahydronaphthyl-1(S)]-ethyl]-4(R)-(t-butyldimethylsilyloxy)-3,4,5,-6-tetrahydro-2H-pyran-2-one (5')

A stirred solution of 4' (15 g, 27.2 mmol) in acetonitrile (300 ml) was treated with a solution prepared from adding 49% hydrofluoric acid (9 ml) to acetonitrile (51 ml) while the temperature was maintained below $-10°$ C. The resulting mixture was stirred for 10 minutes before it was quenched with saturated sodium bicarbonate solution (600 ml) followed by ether extraction. The ethereal extract was washed brine, dried, filtered and evaporated to leave a residue. Purification of the residue by flash chromatography on a silica gel column using 30% ethyl acetate in hexane as the eluant gave the desired product 5' as a gummy oil: nmr (CDCl$_3$) δ 0.09 (6H,s), 0.76 (3H, d, J=7 Hz), 0.83 (3H, t, J=7 Hz), 0.89 (9H, s), 1.02 (3H, d, J=7 Hz), 1.14 (3H, s), 1.15 (3H, s), 3.84 (H, m), 4.30 (H, m), 4.62 (H, m), 5.36 (H, m), 5.72 (H, d, J=6 Hz).

Step 5: Preparation of 6(R)-[2-[3(S)-hydroxy-8(S)-(2,2-dimethylbutyryloxy)-2(R),6(R)-dimethyl-α-4,4a-methyleno-1,2,3,4,4a,5,6,7,8,8a(R)-decahydronaphthyl-1(S)]ethyl]-4(R)-(t-butyldimethylsilyloxy)-3,4,5,6-tetrahydro-2-H-pyran-2-one (6')

To a solution of 5' (15.7 g, 24.9 mmol) in ether (100 ml) was dropwise added a solution of diethylzinc in toluene (1.1m, 33.7 ml, 37 mmol), then diiodomethane (5.51 ml, 18.3 g. 68.4 mmol) via a syringe. The resulting mixture was stirred at ambient temperature for 1 hour, then heated at reflux for 2 hours. After cooling, the reaction mixture was poured into cold 5% hydrochloric acid (600 ml) and extracted with ether. The organic extract was washed with saturated sodium bicarbonate, dried, filtered and evaporated. The residue was purified on a silica gel column eluted with 40% ethyl acetate in hexane to afford the desired 6' as a gummy oil: nmr (CDCl$_3$) δ 0.08 (3H, s), 0.09 (3H, s), 0.52 (H, m), 0.78 (3H, d, J=7 Hz), 0.84 (3H, t, J=7 Hz), 0.87 (9H, s), 1.16 (3H, d, J=7 Hz), 1.17 (6H, s), 4.04 (H, d, J=8 Hz), 4.27 (H, m), 4.55 (H, m), 5.26(H, m).

Step 6: Preparation of 6(R)-[2-[2(R),6(S)-dimethyl-8(S)-(2,2-dimethylbutyryloxy)-α-4,4a-methyleno-1,2,3,4,4a,5,6,7,8,8a(R)-decahydro-3-oxonaphthyl-1(S)]ethyl]-4(R)-(t-butyldimethylsilyloxy)-3,4,5,6-tetrahydro-2H-pyran-2-one (7')

A solution of 6' (9.4 g, 16.6 mmol) in methylene chloride (50 ml) was added via a dropping funnel to a stirred suspension of pyridinium chlorochromate (7.18 g, 33.2 mmol) in methylene chloride (500 ml). The resulting mixture was stirred at ambient temperature for 2 hours, filtered through a layer of celite topped with silica gel. After washing the layer of celite/silica gel with portions of methylene chloride, the combined filtrate and washings were concentrated to yield a residue. Purification of the residue on a silica gel eluted with hexane/ethyl acetate (1.5/1, v/v) gave the desired 7' as a gummy oil: nmr (CDCl$_3$ δ 0.08 (3H, s), 0.09 (3H, s), 0.84 (3H, t, J=7 Hz), 0.89 (9H, s), 1.0 (3H, d, J=7 Hz), 1.17 (6H, s), 1.19 (3H, d, J=7 Hz), 4.28 (H, m), 5.56 (H, m), 5.33 (H, m).

Step 7: Preparation of 6(R)-[2-[2(R),6(S)-dimethyl-8(S)-(2,2-dimethylbutyryloxy)-α-4,4a-methyleno-1,2,3,4,4a,5,6,7,8,8a(R)-decahydro-3-oxonaphthyl-1(S)]ethyl]-4(R)-hydroxy-3,4,5,6-tetrahydro-2H-pyran-2-one (8')

Tetrabutylammonium fluoride solution (1M in THF, 32 ml, 32 mmol) was added to a stirred solution of 7' (7.1 g, 12.6 mmol) and acetic acid (2.3 ml, 40 mmol) in THF (100 ml). The resulting mixture was stirred at ambient temperature for 40 hours, then poured into cold water and extracted with ether. The ethereal extract was washed with 5% sodium bicarbonate, dried, filtered and evaporated to leave a residue. Purification of the residue on a silica gel and eluted with methylene chloride/acetone/i-propanol (50/5/1, v/v/v) provided the desired 8' as a gummy oil. This oil crystallized after trituration with ethyl acetate (10 ml) and hexane (40 ml). Solid 8' was collected by filtration: mp 153°–5° C.; nmr (CDCl$_3$) δ 0.85 (3H, t, J=7 Hz), 1.0 (3H, d, J=7 Hz), 1.17 (6H, s), 1.19 (3H, d, J=7 Hz), 3.61 (H, m of d, J=17 Hz), 2.72 (H, d of d, J=5.17 Hz), 4.37 (H, m), 4.58 (H, m), 5.35 (H, m).

Anal. Calcd for $C_{26}H_{40}O_6$: C, 69.61; H, 8.99; C, 70.00; H, 9.23.

EXAMPLE 2

Preparation of Ammonium Salts of Compounds II

The lactone (1.0 mmol) from Example 1, Step 7' is dissolved with stirring in 0.1N NaOH (1.1 mmol) at ambient temperature. The resulting solution is cooled and acidified by the dropwise addition of 1N HCl. The resulting mixture is extracted with diethyl ether and the extract washed with brine and dried (MgSO$_4$). The MgSO$_4$ is removed by filtration and the filtrate saturated with ammonia (gas) to give a gum which solidified to provide the ammonium salt.

EXAMPLE 3

Preparation of Alkali and Alkaline Earth Salts of Compounds II

To a solution of 44 mg of lactone from Example 1, Step 7, in 2 ml of ethanol is added 1 ml of aqueous NaOH (1 equivalent). After one hour at room temperature, the mixture is taken to dryness in vacuo to yield the desired sodium salt.

In like manner, the potassium salt it prepared using one equivalent of potassium hydroxide, and the calcium salt, using one equivalent of CaO.

EXAMPLE 4

Preparation of Ethylenediamine Salts of Compounds II

To a solution of 0.50 g of the ammonium salt from Example 2 in 10 ml of methanol is added 0.04 ml of ethylenediamine. The methanol is stripped off under vacuum to obtain the desired ehtylenediamine salt.

EXAMPLE 5

Preparation of Tris(hydroxymethyl)aminomethane Salts of Compounds II

To a solution of 202 mg of the ammonium salt from Example 2 in 5 ml of methanol is added a solution of 50 mg of tris(hydroxymethyl)aminomethane is 5 ml of methanol. The solvent is removed in vacuo t afford the desired tris(hydroxymethyl)aminomethane salt.

EXAMPLE 6

Preparation of L-Lysine Salts of Compounds II

A solution of 0.001 mole of L-lysine and 0.0011 mole of the ammonium salt from Example 2 in 15 ml of 85% ethanol is concentrated to dryness in vacuo to give the desired L lysine salt.

15

Similarly prepared are the L-arginine, L-ornithine, and N methylglucamine salts.

EXAMPLE 7

Preparation of Tetramethylammonium Salts of Compounds II

A mixture of 68 mg of ammonium salt from Example 2 in 2 ml of methylene chloride and 0.08 ml of 24% tetramethylammonium hydroxide in methanol is diluted with ether to yield the desired tetramethylammonium salt.

EXAMPLE 8

Preparation Of Methyl Esters of Compounds II

To a solution of 400 mg of lactone from Example 1, Step 7, in 100 ml of absolute methanol is added 10 ml 0.1 M sodium methoxide in absolute methanol. This solution is allowed to stand at room temperature for one hour, then is diluted with water and extracted twice with ethyl acetate. The organic phase is separated, dried ($NaSO_4$), filtered and evaporated in vacuo to yield the desired methyl ester.

In like manner, by the use of equivalent amounts of propanol, butanol, isobutanol, t-butanol, amylalcohol, isoamylalcohol, 2,2-dimethylaminoethanol, benzylalcohol, phenethanol, 2-acetamidoethanol and the like, the corresponding esters are obtained.

EXAMPLE 9

Preparation of Free Dihydroxy Acids

The sodium salt of the compound II from Example 3 is dissolved in 2 ml of ethanol-water (1:1; v:v) and added to 10 ml of 1N hydrochloric acid from which the dihydroxy acid is extracted with ethyl acetate. The organic extract is washed once with water, dried ($Na_2SO_4$), and evaporated in vacuo with a bath temperature not exceeding 30° C. The dihydroxy acid derivative derived slowly reverts to the corresponding, parent lactone on standing. The compound can be maintained in the dihydroxy acid form by increasing th4 pH above 7.0.

EXAMPLE 10

As a specific embodiment of a composition of this invention, 20 mg of lactone from Example 1, Step 7, is formulated with sufficient finely divided lactose to provide a total amount of 580 to 590 mg to fill a size 0, hard-gelatin capsule.

What is claimed is:

1. A compound represented by the structural formulae (I) or (II):

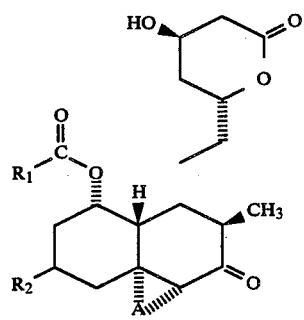

wherein:
$R_1$ is:

(1) $C_{1-10}$ alkyl;
(2) substituted $C_{1-10}$ alkyl in which one or more substituent(s) is
 (a) halogen,
 (b) hydroxy,
 (c) $C_{1-10}$ alkoxy,
 (d) $C_{1-5}$ alkoxycarbonyl,
 (e) $C_{1-5}$ acyloxy,
 (f) $C_{3-8}$ cycloalkyl,
 (g) phenyl,
 (h) substituted phenyl in which the substituents are X and Y,
 (i) $C_{1-10}$ alkylS(O)$_n$,
 (j) $C_{3-8}$ cycloalkylS(O)$_n$,
 (k) phenylS(O)$_n$,
 (l) substituted phenylS(O)$_n$ in which the substituents are X and Y, and
 (m) oxo;
 (n) nitrile,
 (o) $NR_3R_4$,
 (p) $CONR_3R_4$;
(3) $C_{1-10}$ alkoxy;
(4) $C_{2-10}$ alkenyl;
(5) $C_{3-8}$ cycloalkyl;
(6) substituted $C_{3-8}$ cycloalkyl in which one substituent is
 (a) $C_{1-10}$ alkyl
 (b) substituted $C_{1-10}$ alkyl in which the substituent is
  (i) halogen,
  (ii) hydroxy,
  (iii) $C_{1-10}$ alkoxy,
  (iv) $C_{1-5}$ alkoxycarbonyl,
  (v) $C_{1-5}$ acyloxy,
  (vi) phenyl,
  (vii) substituted phenyl in which the substituents are X and Y
  (viii) $C_{1-10}$ alkylS(O)$_n$,
  (ix) $C_{3-8}$ cycloalkylS(O)$_n$,
  (x) phenylS(O)$_n$,
  (xi) substituted phenylS(O)$_n$ in which the substituents are X and Y, and
  (xii) oxo,
 (c) $C_{1-10}$ alkylS(O)$_n$,
 (d) $C_{3-8}$ cycloalkylS(O)$_n$,
 (e) phenylS(O)$_n$,
 (f) substituted phenylS(O)$_n$ in which the substituents are X and Y,
 (g) halogen,
 (h) hydroxy,
 (i) $C_{1-10}$ alkoxy,
 (j) $C_{1-5}$ alkoxycarbonyl,
 (k) $C_{1-5}$ acyloxy,
 (l) phenyl, and
 (m) substituted phenyl in which the substituents are X and Y;
(7) phenyl;
(8) substituted phenyl in which the substituents are X and Y;
(9) amino;
(10) $C_{1-5}$ alkylamino;
(11) di($C_{1-5}$ alkyl)amino;
(12) phenylamino;
(13) substituted phenylamino in which the substituents are X and Y;
(14) phenyl $C_{1-10}$ alkylamino;
(15) substituted phenyl $C_{1-10}$ alkylamino in which the substituents are X and Y;

(16) a member selected from the group consisting of:
  (a) piperidinyl,
  (b) pyrrolidinyl,
  (c) piperazinyl,
$R_2$ is H or $CH_3$;
$R_3$ and $R_4$ are independently selected from:
  (a) $C_{1-5}$ alkyl;
  (b) substituted phenyl in which the substituents are X and Y;
A is $CH_2$;
X and Y are independently selected from:
  (a) OH;
  (b) halogen,
  (c) trifluoromethyl,
  (d) $C_{1-3}$ alkoxy,
  (e) $C_{1-3}$ alkylcarbonyloxy,
  (f) phenylcarbonyloxy,
  (g) $C_{1-3}$ alkoxycarbonyl,
  (h) phenyloxycarbonyl,
  (i) hydrogen,
  (j) $C_{1-5}$ alkyl;

2. A compound of claim 1 wherein:
$R_1$ is selected from:
  (1) $C_{1-10}$ alkyl;
  (2) substituted $C_{1-10}$ alkyl in which one or more substituent(s) is selected from
    (a) halogen,
    (b) hydroxy,
    (c) $C_{1-10}$ alkoxy,
    (d) $C_{1-5}$ alkoxycarbonyl,
    (e) $C_{1-5}$ acyloxy,
    (f) $C_{3-8}$ cycloalkyl,
    (g) phenyl,
    (h) substituted phenyl in which the substituents are X and Y,
    (i) $C_{1-10}$ alkyl $S(O)_n$,
    (j) nitrile,
    (k) $NR_3R_4$,
    (l) $CONR_3R_4$,
    (m) oxo;
  (3) $C_{3-8}$ cycloalkyl;
  (4) substituted $C_{3-8}$ cycloalkyl in which one substituent is selected from
    (a) $C_{1-10}$ alkyl,
    (b) substituted $C_{1-10}$ alkyl in which the substituent is selected from
      (i) halogen,
      (ii) hydroxy,
      (iii) $C_{1-10}$ alkoxy
      (iv) $C_{1-5}$ acyloxy,
      (v) $C_{1-5}$ alkoxycarbonyl,
      (vi) phenyl,
      (vii) substituted phenyl in which the substituents are X and Y, and
      (viii) oxo,
    (c) halogen,
    (d) hydroxy,
    (e) $C_{1-10}$ alkoxy,
    (f) $C_{1-5}$ alkoxycarbonyl,
    (g) $C_{1-5}$ acyloxy,
    (h) phenyl,
    (i) substituted phenyl in which the substituents are X and Y;
  (5) phenylamino;
  (6) substituted phenylamino in which the substituents are X and Y;
  (7) phenyl$C_{1-10}$alkylamino; and
  (8) substituted phenyl $C_{1-10}$ alkylamino in which the substituents are X and Y,
  (9) $C_{2-10}$alkenyl; and
X and Y independently are:
  (a) OH,
  (b) F,
  (c) trifluoromethyl,
  (d) $C_{1-3}$alkoxy,
  (e) hydrogen,
  (f) $C_{1-5}$alkyl.

3. A compound of claim 2 wherein:
$R_1$ is $C_{1-10}$alkyl,
$R^2$ is CH3.

4. A compound of claim 3 selected from the group consisting of:
  (1) 6(R)-[2-[2(R),6(S)-dimethyl-8(S)-(2,2-dimethylbutyryloxy)-α-4,4a-methyleno-1,2,3,4,4a,5,6,7,8,8a(R)-decahydro-3-oxo-naphthyl-1(S)]ethyl]-4(R)-hydroxy-3,4,5,6-tetrahydro-2H-pyran-2-one.

5. A hypocholesterolemic, hypolipidemic pharmaceutical composition comprising a pharmaceutically acceptable carrier and a therapeutically effective amount of a compound as defined in claim 1.

6. A composition of claim 5 in which the compound is selected from:
  (1) 6(R)-[2-[2(R),6(S)-dimethyl-8(S)-(2,2-dimethylbutyryloxy)-α-4,4a-methyleno-1,2,3,4,4a,5,6,7,8,8a(R)-decahydro-3-oxo-naphthyl-1(S)]ethyl]-4(R)-hydroxy-3,4,5,6-tetrahydro-2H-pyran-2-one.

7. A method of treating hypercholesterolemia to a subject in need of such treatment which comprises the administration of an antihypercholestermic effective amount of a compound of claim 1.

8. A method of claim 7 in which the compound is selected from:
  (1) 6(R)-[2-[2(R),6(S)-dimethyl-8(S)-(2,2-dimethylbutyryloxy)-α-4,4a-methyleno-1,2,3,4,4a,5,6,7,8,8a(R)-decahydro-3-oxo-naphthyl-1(S)]ethyl]-4(R)-hydroxy-3,4,5,6-tetrahydro-2H-pyran-2-one.

* * * * *